US008420611B2

(12) United States Patent
Lowenstein et al.

(10) Patent No.: US 8,420,611 B2
(45) Date of Patent: Apr. 16, 2013

(54) COMBINED GENE THERAPY FOR THE TREATMENT OF MACROSCOPIC GLIOMAS

(75) Inventors: Pedro Lowenstein, Los Angeles, CA (US); Maria Castro, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 11/572,391

(22) PCT Filed: Aug. 12, 2005

(86) PCT No.: PCT/US2005/028906
§ 371 (c)(1),
(2), (4) Date: Jan. 28, 2008

(87) PCT Pub. No.: WO2006/020949
PCT Pub. Date: Feb. 23, 2006

(65) Prior Publication Data
US 2008/0181870 A1 Jul. 31, 2008

Related U.S. Application Data

(60) Provisional application No. 60/601,100, filed on Aug. 12, 2004.

(51) Int. Cl.
A61K 48/00 (2006.01)
A01N 63/00 (2006.01)
A01K 67/00 (2006.01)

(52) U.S. Cl.
USPC ............................ 514/44 R; 424/93.2; 800/10

(58) Field of Classification Search ................. 514/44 R; 800/10; 424/93.2
See application file for complete search history.

(56) References Cited

U.S. PATENT DOCUMENTS

| | | | |
|---|---|---|---|
| 5,139,941 A | 8/1992 | Muzyczka et al. | |
| 5,173,414 A | 12/1992 | Lebkowski et al. | |
| 5,501,979 A | 3/1996 | Geller et al. | |
| 5,554,512 A | 9/1996 | Lyman et al. | |
| 5,750,398 A | 5/1998 | Johnson et al. | |
| 5,824,837 A * | 10/1998 | Chen et al. ........................ | 800/3 |
| 6,030,956 A | 2/2000 | Boulikas et al. | |
| 6,066,624 A | 5/2000 | Woo et al. | |
| 6,190,655 B1 | 2/2001 | Lyman et al. | |
| 6,291,661 B1 | 9/2001 | Graddis et al. | |
| 6,365,394 B1 | 4/2002 | Gao et al. | |
| 6,451,593 B1 | 9/2002 | Wittig et al. | |
| 6,518,062 B1 | 2/2003 | Blanche et al. | |
| 6,566,128 B1 | 5/2003 | Graham et al. | |
| 6,630,143 B1 | 10/2003 | Lyman et al. | |
| 6,743,631 B1 | 6/2004 | Mason | |
| 6,818,439 B1 | 11/2004 | Jolly et al. | |
| 6,887,688 B2 | 5/2005 | Lagarias et al. | |
| 7,247,297 B2 | 7/2007 | Weichselbaum et al. | |
| 2003/0031681 A1 | 2/2003 | McCart et al. | |
| 2004/0009588 A1 | 1/2004 | Chang et al. | |
| 2004/0029227 A1 | 2/2004 | Lowenstein et al. | |
| 2004/0191225 A1 | 9/2004 | Dinsmore et al. | |
| 2006/0246038 A1 | 11/2006 | Lowenstein et al. | |
| 2008/0181870 A1 | 7/2008 | Lowenstein et al. | |

FOREIGN PATENT DOCUMENTS

| | | |
|---|---|---|
| AU | 9536584 A | 5/1996 |
| AU | 9536584 B2 | 5/1996 |
| EP | 1786474 B1 | 6/2011 |
| EP | 2338524 A1 | 6/2011 |
| GB | 2355460 A | 4/2001 |
| GB | 2397063 A | 7/2004 |
| WF | WO 93/04167 A1 | 3/1993 |
| WO | WO92/01070 | 1/1992 |
| WO | WO93/03769 | 3/1993 |
| WO | 9509654 A1 | 4/1995 |
| WO | 9509655 A1 | 4/1995 |
| WO | 9612030 A1 | 4/1996 |
| WO | 9620733 A1 | 7/1996 |
| WO | 0065078 A1 | 11/2000 |
| WO | 2006/020949 A3 | 2/2006 |
| WO | 2008/095027 A2 | 8/2008 |

OTHER PUBLICATIONS

Tomasoni and Benigni. Current Gene Therapy 4: 115-122, 2004.*
Gunther et al. Curr. Med. Chem.—Anti-Cancer Agents 5:157-171, 2005.*
Stone et al. J of Endocrinology 164:103-118, 2000.*
Fulci and Chiocca. Expert Opin Biol Ther 7(2): 197. Doi:10.1517/14712598.7.2.197, 2007, pp. 1-18.*
Ali et al., Combined Immunostimulation and Conditional Cytotoxic Gene Therapy Provide Long-Term Survival in a Large Glioma Model, *Cancer Research*, (Aug. 15, 2005), pp. 7194-7204, 65(16).
Ali et al., Inflammatory and Anti-Glioma Effects of an Adenovirus Expressing Human Soluble Fms-Like Tyrosine Kinase 3 Ligand (hsFlt3L): Treatment with hsFlt3L Inhibits Intracranial Glioma Progression, Author Manuscript (published in final version in *Molecular Therapy*, (Dec. 2004), pp. 1071-1084, 10(6)).
Castro et al., Current and Future Strategies for the Treatment of Malignant Brain Tumors, *Pharmacology & Therapeutics*, (2003), pp. 71-108, 98.
Chiocca et al., Viral Therapy for Glioblastoma, *Cancer Journal*, (May-Jun. 2003), pp. 167-179, 9(3).
Cowsill et al., Central Nervous System Toxicity of Two Adenoviral Vectors Encoding Variants of the Herpes Simplex Virus Type 1 Thymidine Kinase: Reduced Cytotoxicity of a Truncated HSV1-TK, *Gene Therapy*, (2000), pp. 679-685, 7.

(Continued)

Primary Examiner — Marcia S Noble
(74) Attorney, Agent, or Firm — Linda B. Huber; Nixon Peabody LLP

(57) ABSTRACT

Described herein are compositions and methods for the treatment of cancer, and particularly brain cancer (e.g., glioma) in a mammal. In various embodiments of the invention, a combined therapeutic approach including TK with systemic ganciclovir administration and Flt3L are used in connection with gene therapeutic techniques or direct peptide injection for the aforementioned indications. Kits useful in practicing the inventive method are also disclosed, as are animal models useful for studying brain cancer.

13 Claims, 2 Drawing Sheets

OTHER PUBLICATIONS

Curtin et al., Fms-Like Tyrosine Kinase 3 Ligand Recruits Plasmacytoid Dendritic Cells to the Brain, *The Journal of Immunology*, (2006), pp. 3566-3577, 176.

Dewey et al., Chronic Brain Inflammation and Persistent Herpes Simplex Virus 1 Thymidine Kinase Expression in Survivors of Syngeneic Glioma Treated by Adenovirus-Mediated Gene Therapy: Implications for Clinica Trials, *Nature Medicine*, (Nov. 1999), pp. 1256-1263, 5(11).

Dong et al., Antitumor Effect of Secreted Flt3L Can Act at Distant Tumor Sites in a Murine Model of Head and Neck Cancer, *Cancer Gene Therapy*, (2003), pp. 96-104,10(2).

Fulci et al., Oncolytic Viruses for the Therapy of Brain Tumors and Other Solid Malignancies: A Review, *Front Bioscience*, (May 1, 2003), pp. 346-360, 8.

Kawashita et al., FLT3-Ligand Gene Transfer Increases Antitumor Effects of Radio-Inducible Suicide Gene Therapy for Hepatocellular Carcinoma, *Proceedings of the Annual Meeting for Cancer Research*, (2001), 42.

Klatzmann et al., A Phase I/II Study of Herpes Simplex Virus Type I Thymidine Kinase "Suicide" Gene Therapy for Recurrent Glioblastoma. Study Group on Gene Therapy for Glioblastoma, *Human Gene Therapy*, (Nov. 20, 1998), pp. 2595-2604, 9(17).

Lang et al., Phase I Trial of Adenovirus-Mediated p53 Gene Therapy for Recurrent Glioma: Biological and Clinical Results, *Journal of Clinical Oncology*, (Jul. 1, 2003), pp. 2508-2518, 21(13).

Lowenstein et al., Immunology of Viral-Vector-Mediated Gene Transfer Into the Brain: An Evolutionary and Developmental Perspective, *Trends in Immunology*, (Jan. 2002), pp. 23-30, 23(1).

Markert et al., Conditionally Replicating Herpes Simplex Virus Mutant, G207 for the Treatment of Malignant Glioma: Results of a Phase I Trial, *Gene Therapy*, (2000), pp. 867-874, 7.

Rainov, N.G., A Phase III Clinical Evaluation of Herpes Simplex Virus Type I Thymidine Kinase and Ganciclovir Gene Therapy As an Adjuvant to Surgical Resection and Radiation in Adults With Previously Untreated Glioblastoma Multiforme, *Human Gene Therapy*, (Nov. 20, 2000), pp. 2389-2401, 11(17).

Rampling et al., Toxicity Evaluation of Replication-Competent Herpes Simplex Virus (ICP 34.5 Null Mutant 1716) in Patients With Recurrent Malignant Glioma, *Gene Therapy*, (May 2000), pp. 859-866, 7(10).

Sandmair et al., Thymidine Kinase Gene Therapy for Human Malignant Glioma, Using Replication-Deficient Retroviruses or Adenoviruses, *Human Gene Therapy*, (Nov. 1, 2000), pp. 2197-2205, 11(16).

Thomas et al., Acute Direct Adenoviral Vector Cytotxicity and Chronic, but Not Acute, Inflammatory Responses Correlate With Decreased Vector-Mediated Transgene Expression in the Brain, *Molecular Therapy*, (Jan. 2001), pp. 36-46, 3(1).

Zermansky et al., Towards Global and Long-Term Neurological Gene Therapy: Unexpected Transgene Dependent, High-Level, and Widespread Distribution of HSV-1 Thymidine Kinase Throughout the CNS, *Molecular Therapy*, (Nov. 2001), pp. 490-498, 4(5).

Final Office Action dated Aug. 14, 2006 for U.S. Appl. No. 10/395,287, filed Mar. 25, 2003, 12 pages.

Written Opinion of the International Searching Authority dated Aug. 15, 2008 for PCT/US2008/52510 filed Jan. 30, 2008,4 pages.

International Preliminary Report on Patentability dated Aug. 4, 2009 for PCT/US08/52510 filed Jan. 30, 2008, 5 pages.

Office Action dated Feb. 19, 2009 for U.S. Appl. No. 11/572,391, filed Jan. 28, 2008, 16 pages.

Final Office Action dated Oct. 13, 2009 for U.S. Appl. No. 11/572,391, filed Jan. 28, 2008,18 pages.

Office Action dated Apr. 29, 2010 for U.S. Appl. No. 11/572,391, filed Jan. 28, 2008,18 pages.

European Search Report dated Oct. 22, 2008 for European patent application No. 05804343.1 (filed Aug. 12, 2005), 9 pages.

Examination Report dated Feb. 2, 2009 for European patent application No. 05804343.1 (filed Aug. 12, 2005), 2 pages.

Examination Report dated Jun. 29, 2010 for European patent application No. 05804343.1 (filed Aug. 12, 2005), 5 pages.

Written Opinion of the International Searching Authority dated Jun. 13, 2006 for PCT/US05/28906 filed Aug. 12, 2005, 6 pages.

International Preliminary Report on Patentability dated Feb. 13, 2007 for PCT/US05/28906 filed Aug. 12, 2005, 7 pages.

Combined Search and Examination Report dated May 6, 2004 for Great Britain patent application No. 0406539.7 (filed Oct. 23, 2000), 8 pages.

Search Report dated Nov. 17, 2000 for Great Britain patent pplication No. 0025890.5 (Oct. 23, 2000), 3 0 pages.

Examination Report dated Aug. 29, 2003 for Great Britain patent application No. 0025890.5 (Oct. 23, 2000), 4 pages.

2nd Examination Report dated Apr. 16, 2004 for Great Britain patent application No. 0025890.5 (Oct. 23, 2000), 1 page.

Office Action dated Sep. 25, 2002 for U.S. Appl. No. 09/693,970, filed Oct. 23, 2000. 16 pages.

Office Action dated Jun. 12, 2002 for U.S Appl. No. 09/693,970, filed Oct. 23, 2000,7 pages.

Office Action dated Apr. 27, 2006 for U.S. Appl. No. 10/395,287, filed Mar. 25, 2003, 7 pages.

Southgate, T. D., et al., "Long-Term Transgene Expression Within the Anterior Pituitary Gland in Situ: Impact on Circulating Hormone Levels, Cellular and Antibody-Mediated Immune Responses", Endrocrinology (2001), 464-476, vol. 142.

Zermansky, A. J., et al., "Towards Global and Long-Term Neurological Gene Therapy: Unexpected Transgene Dependent, High-Level, and Widespread Distribution of SDV-1, Thymidine Kinase Throughout the CNS", Molecular Therapy (2001),490-498, vol. 4.

O'Malley, et al., "The Role of Interleukin-2 in Combination Adenovirus Gene Therapy for Head and Neck Cancer," Mol. Endo. 11(6):667-673 (1997).

U.S. Appl. No. 11/444,050 Non-Final Office Action dated Jun. 28, 2008.

U.S. Appl. No. 11/444,050 Final Office Action dated Apr. 15, 2009.

U.S. Appl. No. 11/444,050 Non-Final Office Action dated Feb. 5, 2010.

U.S. Appl. No. 11/444,050 Final Office Action dated Oct. 15, 2010.

EP 11153885.6 Extended Search Report dated May 27, 2011.

PCT/US08/52510 International Search Report dated Aug. 15, 2008.

PCT/US05/28906 International Search Report dated Jun. 13, 2006.

Blackburn et al., Adenoviral Transduction of a Cytosine Deaminase/ Thymidine Kinase Fusion Gene into Protstate Carcinoma Cells Enhances Prodrug and Radiation Sensitivity. Int. J. Cancer (1999). 82:239-297.

Borelli et al., Targeting of an Inducible Toxic Phenotype in Animal Cells. Proc. Nat'l Acad. Sci. USA (1988), 85:7572-7576.

Ceck E. Cancer fears cast doubts on future gene therapy. Nature. (2003), 1421:p. 6.

Fecci P.E. et al. Viruses in the Treatment of Brain Tumors. Neuroimaging Clin N. Am. (2002), 12(4):553-570.

Felzmann T. et al. Characterization of the antitumor immune response generated by treatment of murine tumors with recombinant adenoviruses expressing HSVtk, IL-2, IL-6 or B7-1. Gene Therapy. (1997), 4:1322-1329.

Galanis E. et al. Use of Viral Fusogenic Membrane Glycoproteins as Novel Therapeutic Transgene in Gliomas. Human Gene Therpay. (2001), 12(7):811-821.

Gansbacher et al., Interleukin 2 Gene Transfer into Tumor Cells Abrogates Tumorigenicity and Induces Protective Immunity. Journal of Experimental Medicine. (1990), 172:1217-1224.

Golumbek et al., Treatment of Established Renal Cancer by Tumor Cells Engineered to Secrete Interleukin-4. Science. (1981), 254(1): 713-716.

Kahle P.J. et al. The emerging utility of animal models of chronic neurodegenerative dieases. Emerging Therapeutic Targets. (2001), 5(1):125-132.

Kawashita Y. et al., A novel therapeutic strategy for hepatocellular carcinoma: Immunomodulation by Flt3-ligand (Flt3L) following whole liver irradiation and radio-inducible HSV-TK gene therapy. International Journal of Radiation Oncology Biology Physics. (2001), 51(2): 105-106 Abstract.

King G.D. et al. Flt3L mediated gene therapy in a syngeneic model of glioma with and without pre-existing adenoviral immunity. Database Biosis (Online) Biosciences Information Service. (2005), 19(5):A1406. Abstract.

Lazic and Barker. Cell-based therapies for disorders of the CNS. Expert Opin. Ther. Patents (2005), 15(10):1361-1370.

Lee et al. Gene transfer into human prostate adenocarcinoma cells with an adenoviral vector: Hyperthermia enhances a double suicide gene expression, cytotoxicity and radiotoxicity. Cancer Gene Therapy. (2002), 9:267-274.

Minasi et al., The Selective Ablation of Interleukin 2-producing Cells Isolated from Transgenic Mice. Journal of Experimental Medicine. (1993), 177:1451-1459.

Russell. Replicating Vectors for Gene Therapy of Cancer: Risks, Limitations and Prospects. European Journal of Cancer. (1994), 30A(8):1165-1171.

Sandmair et al., Thymidine Kinase Gene Therapy for Human Malignant Glioma, Using Replication-Deficient Retroviruses or Adenoviruses. Human Gene Therapy. (2000), 11(16):2197-2205.

Santodonato et al. Local and systemic antitumor response after combined therapy of mouse metastatic tumors with tumor cells expressing IFN-a and HSVtk: perspectives for the generation of cancer vaccines. Gene Therapy. (1997), 4:1246-1255.

Thomas et al. Acute Direct Adenoviral Vector Cytotoxicity and Chronic, but not Acute, Inflammatory Responses Correlate with Decreased Vector-Mediated Transgene Expression in the Brain. Molecular Therapy. (2001), 3(1):36-46.

Thomas et al. Progress and Problems with the use of Viral Vectors for Gene Therapy. Nature. (2003), 4:.346-358.

Tyynela K. et al. Adenovirus mediated herpes simplex virus thymidine kinase therapy in BT4C glioma mode. Cancer Gene Therapy. (2000), 9:917-924.

Verman and Somia. Gene therapy—promises, problems and prospects. Nature. (1997). 389-239-242.

Wang Z. et al. In Vivo and In Vitro Glioma Cell Killing Induced by an Adenovirus Expressing Both Cytosine Deaminase and Thymidine Kinase and its Association with Interferon-a. Journal of Neuropathology and Experimental Neurology (1999), 58(8):847-858.

U.S. Appl. No. 11/444,050 Non-Final Office Action dated Feb. 3, 2012.

U.S. Appl. No. 12/520,500 Non-Final Office Action dated Sep. 1, 2011.

U.S. Appl. No. 12/520,500 Final Office Action dated Jul. 13, 2012.

EP Application No. 11153885.6 Examination Report dated Apr. 11, 2012.

* cited by examiner

COMBINED GENE THERAPY FOR THE TREATMENT OF MACROSCOPIC GLIOMAS

This application is the National Phase of International Application PCT/US05/28906, filed Aug. 12, 2005, which designated the U.S. and that International Application was published under PCT Article 21(2) in English. This application also includes a claim of priority under 35 U.S.C. §119(e) to U.S. provisional patent application No. 60/601,100, filed Aug. 12, 2004.

STATEMENT REGARDING FEDERALLY-SPONSORED RESEARCH

The U.S. Government has a paid-up license in this invention and the right in limited circumstances to require the patent owner to license others on reasonable terms as provided for by the terms of Grant Nos. NS057711, NS061107, and NS052465 awarded by the National Institute on Neurological Disorders and Stroke (NINDS).

FIELD OF THE INVENTION

The invention relates to the field of cancer, and, in particular embodiments, to the treatment of macroscopic gliomas.

BACKGROUND OF THE INVENTION

Brain cancer is a devastating disease and its most common form, glioblastoma multiforme (GBM), is responsible for 50% of all intracranial gliomas and 25% of intracranial tumors in adults. GBM diagnosis carries with it an average survival between twelve and eighteen months (with 90-95% patients surviving less than two years), without the possibility of spontaneous remission or effective treatment. The consistently short survival and absence of spontaneous remission that makes GBM such a devastating disease also render the evaluation of new therapies for this disease relatively rapid and unequivocal—overall survival represents the standard by which therapies for GBM are evaluated. Available treatment options include surgery, radiotherapy and chemotherapy.

Brain tumors are an attractive target for clinical gene therapy using viral vectors because, inter alia, the disease is rapidly fatal and no effective therapies are available [Rainov, N. G., *A phase III clinical evaluation of herpes simplex virus type* 1 *thymidine kinase and ganciclovir gene therapy as an adjuvant to surgical resection and radiation in adults with previously untreated glioblastoma multiforme, Hum Gene Ther,* 11:2389-401 (2000); Lang, F. F. et al., *Phase I trial of adenovirus-mediated p53 gene therapy for recurrent glioma: biological and clinical results, J Clin Oncol,* 21:2508-18 (2003); Sandmair, A. M. et al., *Thymidine kinase gene therapy for human malignant glioma, using replication-deficient retroviruses or adenoviruses, Hum Gene Ther,* 11:2197-205 (2000); Klatzmann, D. et al., *A phase I/II study of herpes simplex virus type* 1 *thymidine kinase "suicide" gene therapy for recurrent glioblastoma,* Study Group on Gene Therapy for Glioblastorna, *Hum Gene Ther,* 9:2595-604 (1998)]. Indeed, gene therapy is an attractive novel therapeutic modality. Viral vectors can transfer genes to relatively large brain areas such as those comprising and surrounding a brain tumor [Chiocca, E. A., et al., *Viral therapy for glioblastoma, Cancer J,* 9:167-79 (2003); Fulci, G. et al., *Oncolytic viruses for the therapy of brain tumors and other solid malignancies: a review, Front Biosci,* 8:346-60 (2003); Castro, M. G. et al., *Current and future strategies for the treatment of malignant brain tumors, Pharmacol Ther,* 98:71-108 (2003)]. In spite of the experimental efficiency of gene therapy, human clinical trials have failed to provide major therapeutic breakthroughs [Rainov, N. G., *A phase III clinical evaluation of herpes simplex virus type* 1 *thymidine kinase and ganciclovir gene therapy as an adjuvant to surgical resection and radiation in adults with previously untreated glioblastoma multiforme, Hum Gene Ther,* 11:2389-401 (2000); Lang, F. F. et al., *Phase I trial of adenovirus-mediated p53 gene therapy for recurrent glioma: biological and clinical results, J Clin Oncol,* 21:2508-18 (2003); Sandmair, A. M. et al., *Thymidine kinase gene therapy for human malignant glioma, using replication-deficient retroviruses or adenoviruses, Hum Gene Ther,* 11:2197-205 (2000); Klatzmann, D. et al., *A phase I/II study of herpes simplex virus type* 1 *thymidine kinase "suicide" gene therapy for recurrent glioblastoma,* Study Group on Gene Therapy for Glioblastorna, *Hum Gene Ther,* 9:2595-604 (1998)]. One shortcoming of previous clinical trials is that they necessarily concentrate on single therapeutic approaches (e.g., conditional cytotoxicity or immunotherapy). Further, microscopic brain tumor models used experimentally may not reflect faithfully large human tumors.

There thus remains a need in the art for effective treatments for brain cancer that obviates the aforementioned limitations, and takes advantage of gene therapeutic and direct peptide injection techniques.

The disclosures of all documents referred to throughout this application are incorporated herein by reference. The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other improvements.

An embodiment of the present invention includes a method for treating cancer in a mammal by providing a viral vector expressing TK and a viral vector expressing Flt3L, administering a therapeutically effective amount of the vectors to the mammal, and administering a therapeutically effective quantity of systemic ganciclovir to the mammal. The vectors may be independently selected from a wide range of vectors, although in particular embodiments the TK viral vector is HSV-1 and the Flt3L vector is a recombinant adenoviral vector. The cancer may be brain cancer.

Another embodiment of the present invention includes a method for treating cancer in a mammal by providing a viral vector expressing TK, providing a composition including Flt3L protein, administering therapeutically effective amounts of the same to the mammal, and administering a therapeutically effective quantity of systemic ganciclovir to the mammal. The vector may be selected from a wide range of vectors, although in some embodiments the TK viral vector is HSV-1. The cancer may be brain cancer.

Another embodiment of the present invention includes a kit, comprising a composition comprising a viral vector expressing TK, a composition comprising a viral vector expressing Flt3L, and instructions for their use in treating cancer in a mammal. The kit may also contain a quantity of ganciclovir.

Another embodiment of the present invention includes a kit, comprising a composition comprising a viral vector expressing TK, a composition comprising Flt3L peptide, and instructions for their use in treating cancer in a mammal. The kit may also contain a quantity of ganciclovir.

Another embodiment of the present invention includes an animal model for brain cancer, including a non-human mammal that carries in at least a portion of the cells of its brain at least one exogenous TK DNA and at least one exogenous Flt3L DNA.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures of the drawings. It is intended that the embodiments and figures disclosed herein are to be considered illustrative rather than restrictive.

DETAILED DESCRIPTION

Figure 1:
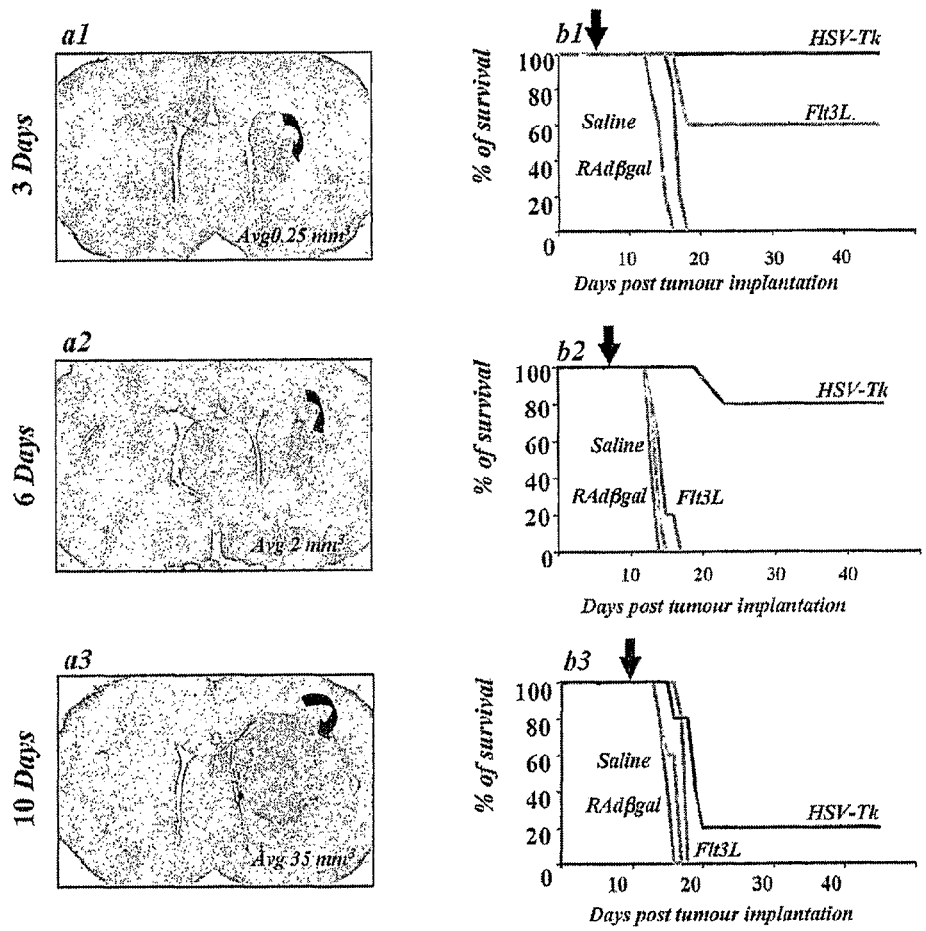
FIG. 1 illustrates (a1-3) tumor sizes at 3, 6 and 10 days post CNS1 cell implantation, in accordance with an embodiment of the present invention. Brains were stained with ED1 antibody, which outlines tumor area. With time the tumours increased in size, and remained localized to the hemisphere of injection as indicated by the arrows. (b1-3) Efficiency of $8\times10^7$ pfu of either RAdTK+ganciclovir (GCV) or RAdFlt3L in inhibiting the growth of tumors of different sizes.
Figure 2:
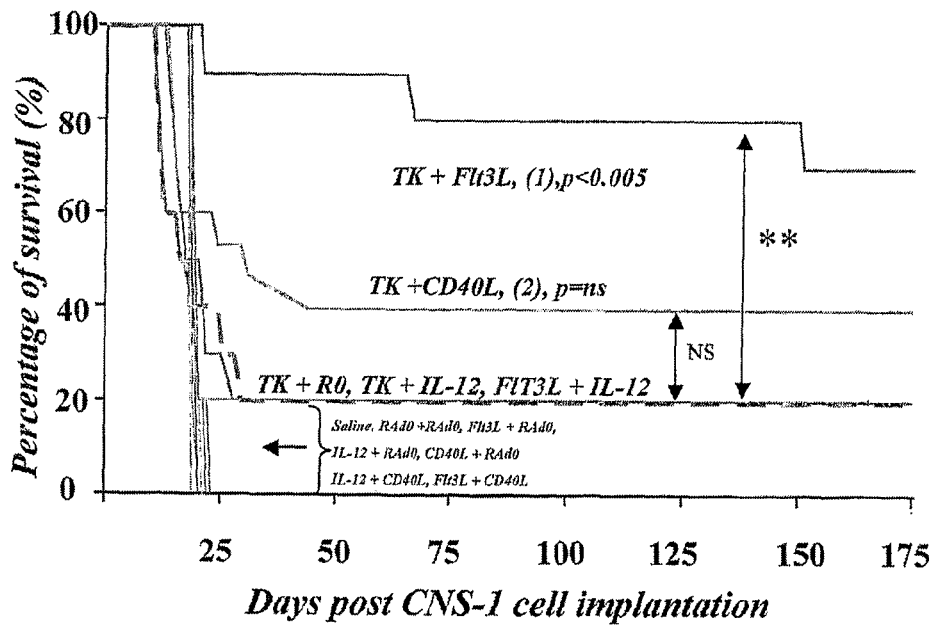
FIG. 2 illustrates the survival of animals with macroscopic tumors treated on day 10 with RAdTK+GCV ($1\times10^7$ pfu) and RAdFlt3L/RAdCD40L/RAdIL-12 ($1\times10^7$ pfu) and all necessary control groups as indicated, in accordance with an embodiment of the present invention. Each of the therapeutic viruses combined with RAdO ($1\times10^7$ pfu) were used as further controls. Following intra-tumoral injection of virus the animals were injected twice daily with 25 mg/kg GCV for seven days.
Figure 3:
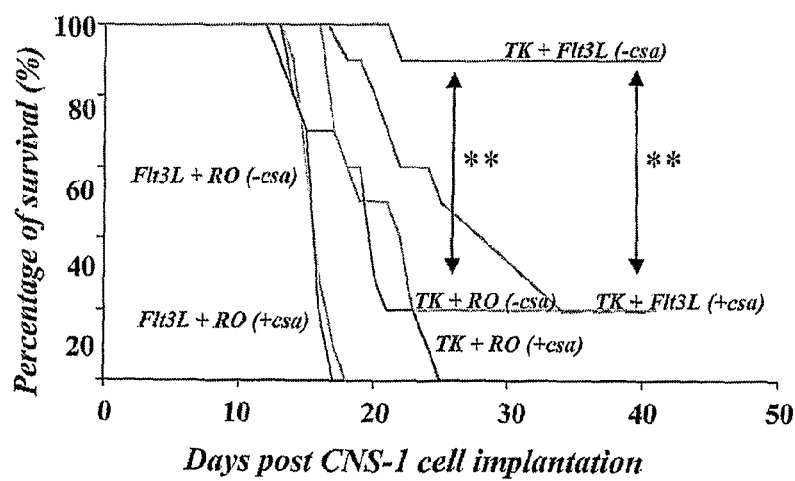
FIG. 3 illustrates survival of immunosuppressed animals with macroscopic tumors treated on day 10 with RAdTK+GCV ($1\times10^7$ pfu) and RAdFlt3L ($1\times10^7$ pfu) and all necessary control groups as indicated, in accordance with an embodiment of the present invention. Following intra-tumoral injection of virus the animals were injected twice daily with 25 mg/kg GCV for seven days. Immunosuppression was started on day seven and continued for the entire experiment. Animals received 10 mg/kg cyclosporin A, given orally by gavage twice daily.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994); March, *Advanced Organic Chemistry Reactions, Mechanisms and Structure* 4th ed., J. Wiley & Sons (New York, N.Y. 1992); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" include, but are in no way limited to, lessening or alleviating the severity of cancer (e.g., gliomas) or its complications, preventing or inhibiting it from manifesting, preventing or inhibiting it from recurring, merely preventing or inhibiting it from worsening, curing cancer, reversing the progression of cancer, prolonging a patient's life or life expectancy, ameliorating cancer, or a therapeutic effort to effect any of the aforementioned, even if such therapeutic effort is ultimately unsuccessful.

"Curing" brain cancer includes altering the physiology of the central nervous system ("CNS") and/or its biological components to the point that the disease cannot be detected after treatment.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346. Examples of well known vehicles for gene transfer include adenovirus and recombinant adenovirus (RAd), adeno-associated virus (AAV), herpes simplex virus type 1 (HSV-1), and lentivirus (LV).

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Therapeutically effective amount" as used herein refers to that amount which is capable of achieving beneficial results in a patient with cancer, such as glioma. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease even if the treatment is ultimately unsuccessful.

"AAV vector" refers to any vector derived from an adeno-associated virus serotype, including, without limitation, AAV-1, AAV-2, AAV-3, AAV-4, AAV-5, AAVX7, etc. AAV vectors can have one or more of the AAV wild-type genes deleted in whole or in part, preferably the Rep and/or Cap genes, but retain functional flanking inverted terminal repeat ("ITR") sequences. Functional ITR sequences are generally necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging. A number of adenovirus-based gene delivery systems have also been developed. Human adenoviruses are double-stranded DNA viruses which enter cells by receptor-mediated endocytosis. These viruses are particularly well suited for gene transfer because they are easy to grow and manipulate and they exhibit a broad host range both in vivo and in vitro. Adenovirus is easily produced at high titers and is stable so that it can be purified and stored. Even in the replication-competent form, adenoviruses generally cause only low level morbidity and are generally not associated with human malignancies. For descriptions of various adenovirus-based gene delivery systems, see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476. The construction of recombinant adeno-associated virus ("rAAV") vectors has also been described. See, e.g., U.S. Pat. Nos. 5,173,414 and 5,139,941; International Patent Publication Numbers WO 92/01070 (published Jan. 23, 1992) and WO 93/03769 (published Mar. 4, 1993); Lebkowski et al. *Molec. Cell. Biol.* 8:3988-3996 (1988); Vincent et al., *Vaccines* 90 (Cold Spring Harbor Laboratory Press) (1990); Carter, B. J. *Current Opinion in Biotechnology* 3:533-539 (1992); Muzyczka, N., *Current Topics in Microbiol. and Immunol.* 158:97-129 (1992); and Kotin, R. M. *Human Gene Therapy* 5:793-801 (1994).

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious.

A "recombinant AAV virion" or "rAAV virion" is defined herein as an infectious, replication-defective virus composed of an AAV protein shell, encapsidating a heterologous DNA molecule of interest (e.g., TK, Flt3L) which is flanked on both sides by AAV ITRs. A rAAV virion may be produced in a suitable host cell which has had an AAV vector, AAV helper functions and accessory functions introduced therein. In this manner, the host cell is rendered capable of encoding AAV polypeptides that are required for packaging the AAV vector (i.e., containing a recombinant nucleotide sequence of interest) into recombinant virion particles for subsequent gene delivery.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. *Virology*, 52:456 (1973); Sambrook et al. *Molecular Cloning, a laboratory manual*, Cold Spring Harbor Laboratories, New York (1989); Davis et al., *Basic Methods in Molecular Biology*, Elsevier (1986), and Chu et al. *Gene* 13:197 (1981). Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

The term "heterologous," as it relates to nucleic acid sequences such as gene sequences and control sequences, denotes sequences that are not normally joined together and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

"DNA" is meant to refer to a polymeric form of deoxyribonucleotides (i.e., adenine, guanine, thymine and cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine and cytosine, as well as molecules that include base analogues which are known in the art.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences. The boundaries of the gene are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

"Homology" as used herein refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA or two polypeptide sequences are "substantially homologous" to each other when at least about 80%, preferably at least about 90%, and most preferably at least about 95% of the nucleotides or amino acids, respectively, match over a defined length of the molecules, as determined using the methods above.

"Isolated" as used herein when referring to a nucleotide sequence, refers to the fact that the indicated molecule is present in the substantial absence of other biological macromolecules of the same type. Thus, an "isolated nucleic acid molecule which encodes a particular polypeptide" refers to a nucleic acid molecule that is substantially free of other nucleic acid molecules that do not encode the subject polypeptide. However, the molecule may include some additional bases or moieties that do not deleteriously affect the basic characteristics of the composition.

The present invention is based on a combined gene therapy approach that was tested in a stringent macroscopic brain tumor model. In this model, single therapeutic modalities, such as conditional cytotoxicity and immune stimulation, administered on their own, fail. Importantly, the inventors found that combined delivery of Flt-3L and HSV1-TK/ganciclovir, however, does prolong survival in the majority of animals bearing a macroscopic tumor at the time of treatment. This novel therapeutic approach has been tested in a stringent pre-clinical model, as described in greater detail in the ensuing Examples.

The invention includes compositions and methods for the treatment of cancer, and in particular, brain cancer (more particularly, glioma), using a combined therapy of Flt-3L and HSV1-TK/ganciclovir, either through entirely gene therapeutic approaches or a gene therapeutic approach also involving direct peptide injection (i.e., direct peptide injection of Flt-3L combined with gene therapy using HSV1-TK/ganciclovir). More specifically, the invention includes methods of treating brain cancer by administering a therapeutically effective amount of Flt-3L and HSV1-TK/ganciclovir to a mammal in individually appropriate dosing regimens, respectively. In one embodiment of the present invention, the mammal is a human. The therapeutic components may be formulated into appropriate pharmaceutical compositions for use in connection with the gene therapeutic and/or direct peptide delivery techniques as contemplated by alternate embodiments of the present invention.

The inventive therapeutics may be administered by any appropriate technique, as will be readily appreciated by those of skill in the art. For instance, any suitable gene therapeutic approach may be implemented to deliver the DNA of interest in accordance with various embodiments of the present invention. In one embodiment of the present invention, a HSV-1 vector is used to deliver TK to target cells (e.g., in the brain), and ganciclovir is systemically administered. Additionally, Flt-3L may be delivered to target cells (e.g., in the brain) by any number of techniques as will be readily appreciated by those of skill in the art. By way of example, Flt-3L protein may be delivered by direct peptide injection or it may be administered via a gene therapeutic approach; for instance, through the use of a RAd vector (e.g., RAd-Flt3L).

More particularly, in connection with another embodiment of the present invention, HSV-1, rAd, rAAV, etc. virions including heterologous DNA corresponding to a TK and/or Flt3L coding sequence may be generated by any conventional technique known in the art. By way of example, recombinant virions of the present invention, including the TK or Flt3L DNA of interest, can be produced by a standard methodology that generally involves the steps of: (1) introducing a viral vector into a host cell; (2) introducing a helper construct into the host cell, where the helper construct includes coding regions capable of being expressed in the host cell to complement helper functions missing from the vector; (3) introducing one or more helper viruses and/or accessory function vectors into the host cell, wherein the helper virus and/or accessory function vectors provide accessory functions capable of supporting efficient recombinant virion production in the host cell; and (4) culturing the host cell to produce recombinant viral virions. The vector, helper construct and the helper virus or accessory function vector(s) can be introduced into the host cell either simultaneously or serially, using standard transfection techniques. Examples of such techniques are described in greater detail in the ensuing Examples herein.

Vectors are constructed using known techniques to at least provide, as operatively linked components in the direction of transcription, (a) control elements including a transcriptional initiation region, (b) the DNA of interest and (c) a transcriptional termination region. Moreover, any coding sequence sufficiently homologous to the TK and/or Flt3L coding sequence so as to exhibit functional properties substantially similar to the TK and/or Flt3L coding sequence, respectively, may be used in connection with alternate embodiments of the present invention. The control elements are selected to be functional in the targeted cell(s). The resulting construct, which contains the operatively linked components, may be bounded (5' and 3') with functional ITR sequences. The nucleotide sequences of, for example, AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including, without limitation, AAV-1, AAV-2, AAV-3, AAV-4, AAV-5, AAVX7, and the like. Furthermore, 5' and 3' ITRs that flank a selected nucleotide sequence in an AAV expression vector need not necessarily be identical or derived from the same AAV serotype or isolate, so long as they function as intended (i.e., to allow for excision and replication of the bounded nucleotide sequence(s) of interest).

Therefore, in accordance with an embodiment of the invention, the virions including a TK and/or Flt3L coding sequence are delivered to a mammal in a sufficient quantity and by a sufficient delivery route so as to effect gene transfer. This may provide an effective treatment for cancer, and specifically brain cancer, in the mammal; particularly when implemented in connection with the systemic administration of ganciclovir.

In an alternate embodiment of the present invention, a quantity of Flt3L peptide may be directly administered to a mammal (e.g., to the brain) in the aforementioned combined approach and in a therapeutically effective amount so as to treat cancer, and particularly brain cancer.

In various embodiments, the present invention provides pharmaceutical compositions (in connection with gene therapeutics and direct peptide administration techniques) including a pharmaceutically acceptable excipient along with either a therapeutically effective amount of a viral vector for delivery of TK and/or Flt3L or a therapeutically effective amount of Flt3L protein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. In one embodiment of the present invention the inventive compositions are injected directly into the brain of a mammal.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosages and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

The present invention is also directed to a kit for the treatment of cancer, and in particular, brain cancer. The kit is useful for practicing the inventive methods. The kit is an assemblage of materials or components, including at least one of the inventive compositions. Thus, in some embodiments the kit contains compositions including viral vectors expressing TK and Flt3L, respectively, or, in an alternate embodiment, the kit contains a composition including a viral vector expressing TK and a composition including Flt3L peptides, as described above. In either instance, a quantity of ganciclovir may also be included.

The exact nature of the components configured in the inventive kit depends on its intended purpose. For example, some embodiments of the kit are configured for the purpose of treating cultured mammalian cells. Other embodiments are configured for the purpose of treating mammalian cells in vivo (i.e., for treating mammalian subjects in need of treatment, for example, subjects with cancer). In one embodiment, the kit is configured particularly for the purpose of treating human subjects.

Instructions for use may be included in the kit. "Instructions for use" typically include a tangible expression describing the technique to be employed in using the components of the kit to effect a desired outcome, such as the treatment of cancer, and particularly, brain cancer. Optionally, the kit also contains other useful components, such as, diluents, buffers, pharmaceutically acceptable carriers, specimen containers, syringes, stents, catheters, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in polynucleotide-based or peptide-based systems. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing nucleic acid or peptide components. The packaging material generally has an external label which indicates the contents and/or purpose of the kit and/or its components.

In another embodiment, the present invention includes various in vivo models of brain cancer, using a non-human mammal that carries in at least a portion of the cells of its brain at least one exogenous TK and one exogenous Flt3L DNA. Such animal models may be useful for a variety of purposes, including studying a number of diseases and physiologic conditions (e.g., those described herein), as well as screening therapeutic candidates for the treatment of such diseases and physiologic conditions, and still further uses that will be readily apparent to those of skill in the art.

The inventors generated adenoviral vectors expressing either Flt3L (RAd-Flt3L) or HSV1-TK (RAd128), and tested these for bioactivity in vitro and in vivo. In vitro experiments indicated that supernatant of RAd-Flt3L infected cells increased the migratory activity of monocyte-derived dendritic cells (DC). In vivo injection of RAd-Flt3L into the brains of mice caused a very significant up-regulation of MHC-II expression throughout the ipsilateral brain hemisphere, and increased the presence within the mouse brain of cells expressing markers of monocyte-derived DCs, such as 33D1 and CD11c, but not markers of lymphoid-derived DCs, such as DEC205 (data not shown). In the rat brain, RAd-Flt3L induced the expression of OX-62, a marker specific to DC and γ6-Tcells. Adenoviral vectors expressing CD40L9 and IL-1210 were generated and tested as described elsewhere [Sun, Y. et al., *In vivo gene transfer of CD40 ligand into colon cancer cells induces local production of cytokines and chemokines, tumor eradication and protective antitumor immunity*, Gene Ther, 7:1467-76 (2000); Lasarte, J. J. et al., *Different doses of adenoviral vector expressing IL-12 enhance or depress the immune response to a coadministered antigen: the role of nitric oxide*, J Immunol, 162:5270-7 (1999)].

The inventors had previously characterized and established a powerful syngeneic animal model of glioma brain tumors using the injection of CNS1 cells into the brains of Lewis rats. They had successfully used this model to demonstrate the powerful effect of HSV1-TK and systemic ganciclovir in eliminating syngeneic tumors, and permitting long-term survival. In addition, in this model system, in parallel with the therapeutic efficiency, they also detected short- and long-term adverse side effects in the brains of the long-term surviving animals [Dewey, R A. et al., *Chronic brain inflammation and persistent herpes simplex virus 1 thymidine kinase expression in survivors of syngeneic glioma treated by adenovirus-mediated gene therapy: implications for clinical trials*, Nat Med, 5:1256-63 (1999)]. Other experimental gene therapies include the expression of tumor suppressors, oncogene inhibitors, angiogenesis inhibitors, immune-stimulatory approaches, and more recently the use of replication-competent viral vectors, such as those based on HSV-1 [Sandmair, A. M. et al., *Thymidine kinase gene therapy for human malignant glioma, using replication-deficient retroviruses or adenoviruses*, Hum Gene Ther, 11:2197-205 (2000); Klatzmann, D. et al., *A phase I/II study of herpes simplex virus type 1 thymidine kinase "suicide" gene therapy for recurrent glioblastoma*, Study Group on Gene Therapy for Glioblastorna, Hum Gene Ther, 9:2595-604 (1998); Fulci, G. et al., *Oncolytic viruses for the therapy of brain tumors and other solid malignancies: a review*, Front Biosci, 8:346-60 (2003); Rampling, R. et al., *Toxicity evaluation of replication-competent herpes simplex virus (ICP 34.5 null mutant 1716) in patients with recurrent malignant glioma*, Gene Ther, 7:859-66 (2000); Markert, L M. et al., *Conditionally replicating herpes simplex virus mutant, G207 for the treatment of malignant glioma: results of a phase I trial*, Gene Ther, 7:867-74 (2000); Rainov, N. G. et al., *Vector delivery methods and targeting strategies for gene therapy of brain tumors*, Curr Gene Ther, 1:367-83 (2001)]. In spite of all these approaches being successful in microscopic brain tumor models, their effectiveness needs to be stringently assessed in a representative, truly macroscopic intracranial glioma model. A macroscopic model is critical in order to assess the efficacy of gene therapy approaches, in a relevant preclinical model, as described herein.

A number of these tumor-killing approaches have been tested in phase I/II clinical trials, with only one trial progressing a phase III/IV [1]. In the clinical setting, none of these approaches provided the expected breakthroughs, although some trials indicated sufficient clinical efficacy to justify further pursuit [Rainov, N. G.; *A phase III clinical evaluation of herpes simplex virus type 1 thymidine kinase and ganciclovir gene therapy as an adjuvant to surgical resection and radiation in adults with previously untreated glioblastoma multiforme*, Hum Gene Ther, 11:2389-401 (2000); Sandmair, A. M. et al., *Thymidine kinase gene therapy for human malignant glioma, using replication-deficient retroviruses or adenoviruses*, Hum Gene Ther, 11:2197-205 (2000); Klatzmann, D. et al., *A phase I/II study of herpes simplex virus type 1 thymidine kinase "suicide" gene therapy for recurrent glioblastoma*, Study Group on Gene Therapy for Glioblastorna, Hum Gene Ther, 9:2595-604 (1998); Rampling, R. et al., *Toxicity evaluation of replication-competent herpes simplex virus (ICP 34.5 null mutant 1716) in patients with recurrent malignant glioma*, Gene Ther, 7:859-66 (2000); Markert, L M. et al., *Conditionally replicating herpes simplex virus mutant, G207 for the treatment of malignant glioma: results of a phase I trial*, Gene Ther, 7:867-74 (2000)]. The dissociation between encouraging experimental efficiency and limited successes in clinical trials, although frustrating, is not unexpected based on previous experience in fields such as stroke therapeutics. Potential explanations for this apparent paradox center on the limitations of available experimental animal models.

The models used in previous studies consisted of glioma cell lines, maintained in culture, and injected into the animals' flank or brain. Therapies are usually administered within less than three days of tumor implantation (i.e., when the tumor mass is very small (FIG. 1, a1)). These cells grow into mass lesions, which eventually kill the animals.

Novel models have thus been developed to overcome the intrinsic limitations of experimental brain tumor models for the development of novel treatments for human gliomas [Fulci, G. et al., *Oncolytic viruses for the therapy of brain tumors and other solid malignancies: a review*, Front Biosci, 8:346-60 (2003); Castro, M. G. et al., *Current and future strategies for the treatment of malignant brain tumors*, Pharmacol Ther, 98:71-108 (2003); Holland, E. C., *Gliomagenesis: genetic alterations and mouse models*, Nat Rev Genet, 2:120-9 (2001)]. Improving brain tumor animal models is a concern to the scientific community, as better models of tumor pathophysiology and tumor treatments are badly needed. As a result, a number of transgenic mouse models have been developed [Holland, E. C., *Gliomagenesis: genetic alterations and mouse models*, Nat Rev Genet, 2:120-9 (2001)]. These are transgenic knockout, or compound knockout animal models, in which brain tumors can be detected. Although these models have kindled much interest in the field, they may have a stronger impact for the understanding of the pathophysiology of brain tumors than for the development of novel experimental therapies. This is due to the fact that the tumors develop at different stages during the lifespan of the animals and also, for efficacy studies the tumors have to be of similar size at the time of experimental treatment. So far, this has not been possible to achieve using the transgenic brain tumor models.

Therefore, the inventors used the CNS-1 tumor model in Lewis rats for the following characteristics and advantages over other available models: (i) CNS1 cells are derived from Lewis rats and are thus syngeneic in this rat strain; (ii) these cells have a reproducible growth rate and life span from implantation to death; and (iii) the tumors are susceptible to experimental gene therapies [Dewey, R A. et al., *Chronic brain inflammation and persistent herpes simplex virus 1 thymidine kinase expression in survivors of syngeneic glioma treated by adenovirus-mediated gene therapy: implications for clinical trials*, Nat Med, 5:1256-63 (1999); Cowsill, C. et al., *Central nervous system toxicity of two adenoviral vectors encoding variants of the herpes simplex virus type 1 thymidine kinase: reduced cytotoxicity of a truncated HSV1-TK*, Gene Ther, 7:679-85 (2000)]. In addition, Lewis rats are susceptible to the induction of experimental allergic encephalomyelitis and thus provide a powerful model in which to assess long term inflammatory side effects of novel therapies, potential serious adverse side effects of immunotherapies, should they serve to eradicate the brain tumors.

Previously, the inventors used a model in which 5,000 cells were implanted unilaterally into the striatum and, three days later, experimental gene therapies in the form of adenoviral vectors were injected into the same site of the striatum. In such a model, the delivery of RAd128 (hCMV-HSV1TK) followed by seven days of systemic ganciclovir rescued 100% of animals from death [Dewey, R A. et al., *Chronic brain inflammation and persistent herpes simplex virus 1 thymidine kinase expression in survivors of syngeneic glioma treated by adenovirus-mediated gene therapy: implications for clinical trials*, Nat Med, 5:1256-63 (1999)]. These animals survive very long term without any clinical or anatomical evidence of glioma progression. In the same model, injection of RAd-Flt3L rescued approximately 60% of animals (FIG. 1, b1). However, in the clinic, HSV1-TK/GCV has not been as effective, and Flt3L was heretofore untested in glioma models.

The inventors thus decided to make their model more stringent. To do so, they opted to deliver gene therapies into much larger tumors, by injecting the therapeutic viruses when the tumors were truly macroscopic and occupying most of the brain's hemisphere. A tumor of this size is detected at ten days post implantation of 5,000 CNS 1 cells. Tumor size was determined over several days. Three days after injection of 5,000 CNS1 cells, tumors averaged 0.25 mm$^3$, 2 mm$^3$ after six days, and 35 mm$^3$ after ten days (FIG. 1*a*1-3). Death of untreated or control animals occurred approximately at 20-25 days post-tumor cell implantation. Treatment with adenovirus expressing HSV1-TK at three days after tumor implantation, and systemic delivery of GCV for seven days, rescued all animals from death as previously demonstrated (FIG. b1), whilst injection of a vector expressing Flt3L protected approximately 60% of animals from death assessed up to six months after tumor implantation if gene therapy was delivered at six days, injection of RAdFlt3L became ineffective, while RAdTK/GCV lost approximately 20% of its efficiency, protecting only 80% of animals, while at ten days it lost 80% of its efficiency, only protecting 20% of the animals. Thus, this model now reproduces more closely the human paradigm: tumors are macroscopic at the time of treatment, and single gene therapies are only marginally effective.

DCs are absent from the naïve brain, but are detected within the brain under conditions that cause brain inflammation [Lowenstein, P. R., *Immunology of viral-vector-mediated gene transfer into the brain: an evolutionary and developmental perspective*, Trends Immunol, 23:23-30 (2002); McMenamin, P. G., *Distribution and phenotype of dendritic cells and resident tissue macrophages in the dura mater, leptomeninges, and choroid plexus of the rat brain as demonstrated in wholemount preparations*, J Camp Neurol, 405:553-62 (1999); Fischer, H. G. et al., *Brain dendritic cells and macrophages/microglia in central nervous system inflammation*, J Immunol, 166:2717-26 (2001); Fischer, H. G. et al., *Phenotype and functions of brain dendritic cells emerging during chronic infection of nice with Toxoplasma gondii*, J Immunol, 164:4826-34 (2000); Santambrogio, L. et al., *Developmental plasticity of CNS microglia*, Proc Natl Acad Sci USA, 98:6295-300 (2001); Serafini, B. et al., *Intracerebral recruitment and maturation of dendritic cells in the onset and progression of experimental autoimmune encephalomyelitis*, Am J Pathol, 157:1991-2002 (2000)]. The lack of DCs from the brain could help explain, in part, the failure to stimulate an anti-tumor immune response in the brain. In the macroscopic model the inventors decided to co-deliver both RAd-TK/GCV as well as a number of immune-stimulatory agents that would either increase the number of dendritic cells (e.g., Flt3L) [Banchereau, J. et al., *Dendritic cells as vectors for therapy*, Cell, 106:271-4 (2001)], activate DCs (e.g., CD40L) [Zou, G. M. et al., *Cytokines in the generation and maturation of dendritic cells: recent advances*, Eur Cytokine Netw, 13:186-99 (2002)], or stimulate the immune responsiveness of various immune cell types (e.g., IL-12) [Puccetti, P. et al., *Effects of IL-12 and IL-23 on antigen-presenting cells at the interface between innate and adaptive immunity*, Crit Rev Immunol, 22:373-90 (2002); Banchereau, J. et al., *Dendritic cells: controllers of the immune system and a new promise for immunotherapy*, Ann N Y Acad Sci, 987:180-7 (2003)]. The theory underlying these experiments was that killing of tumor cells with HSVI-TK/GCV would provide antigenic tumor epitopes to DCs in situ. These DCs would either be recruited to the brain and/or stimulated through the administration of the specific gene therapies. DCs leaving the brain would eventually stimulate an adaptive immune response resulting in the elimination of tumor and enhanced survival of tumor-bearing animals.

In subsequent studies, groups of animals were injected ten days post tumor implantation, with Flt3L, IL-12, CD40L, or combinations of 1L-12+CD40L, and Flt3L+CD40L. All these treatments were ineffective in prolonging animal survival and tumor elimination compared to controls. HSV1-TK/GCV only protected 20% of animals; this protection was not increased by the addition of IL 12, and similar results were obtained after treating the animals with Flt3L plus IL-12. None of these treatments were statistically different from controls. Treatment with HSV1-TK/GCV plus CD40L rescued 40% of the animals; this increase, however, failed to reach statistical significance compared to animals treated with HSV1-TK/GCV on its own.

The combined treatment with HSV1-TK/GCV and Flt3L however, rescued a highly significant percentage of animals from death. Even as late as six months after tumor implantation, greater than 70% of animals remained alive, compared to animals in all control groups that were all dead by day 25 post tumor implantation. The inventors' studies indicate that conditionally cytotoxic brain tumor killing with HSV1-TK/GCV of a large tumor occupying most of the ipsilateral hemisphere, in combination with the DC growth factor Flt3L is able to provide an efficacious therapeutic approach for improving the outcome of otherwise untreatable brain tumors in a syngeneic intracranial animal model.

The administration of powerful pro-inflammatory/immune-stimulatory agents might induce systemic anti-CNS immune responses that may cause serious side effects that could compromise the therapy's efficiency. To determine this, spinal cords of animals in different groups and that had survived up to 6 months (illustrated in FIG. 2) were analyzed to determine the presence and distribution of inflammatory infiltrates (T-cells and macrophages) in the meninges, and within the spinal cords. Inflammatory infiltrates of T cells across all groups was very low (10-30 cells/section), but higher than normal control animals (0-2 T cells per section). In one animal (injected with TK+IL12) a few typical perivascular inflammatory infiltrates were found, similar in quantity to those found in very mild subclinical EAE. No animal displayed overt symptoms of EAE. The distribution of macrophages throughout the spinal cord, and especially throughout the cortico-spinal tract indicates a lesion in the pyramidal tract, most likely explained by a lesion to the capsula interna due to the tumor or even a small lesion to the pyramidal tract. Even a direct or indirect (compression) lesion to the capsula interna, where the pyramidal tract is located in the forebrain, will produce visible lesions within the corticospinal tract in the spinal cord. As a general conclusion, overt signs compatible with full blown EAE were not detected, but a very low level of T cell infiltration of the meninges and spinal cord lesions due to degenerating axons in the cortico-spinal were detected, most likely explained by the tumor or a small lesion to the pyramidal tract in the forebrain.

The inventors postulated that if the combined gene therapy of Flt3L+HSV1TK/GCV is acting through an immune-stimulatory mechanism, immune suppression of these animals should inhibit the therapeutic effects of the combined treatment. The experiment was therefore repeated, and groups of animals were treated with Cyclosporin-A twice daily [Guillot, C. et al., *Lethal hepatitis after gene transfer of IL-4 in the liver is independent of immune responses and dependent on apoptosis of hepatocytes: a rodent model of IL-4-induced hepatitis, J Immunol,* 166:5225-35 (2001)]. Levels of serum Cyclosporin-A were measured and were above clinical doses according to standard clinical medical and laboratory practice. Cyclosporin-A treatment did not have a significant effect on the life span of any of the control animals, but completely abolished the survival provided by HSVI-TK/GCV combined with Flt3L. At 40 days post-tumor implantation, and 30 days post-gene therapy, in animals immune-suppressed with Cyclosporin-A survival of animals treated with both HSV1-TK and Flt3L was reduced to the level of survival of animals treated with HSV1-TK/GCV alone. Thus, it is believed that the beneficial therapeutic effects of HSV1-TK/GCV+Flt3L in the macroscopic glioma model is sensitive to immune-suppression by Cyclosporin-A.

The impetus for these studies was to discover new approaches for the experimental and clinical gene therapy for brain tumors. Although the inventors' "small" CNS1 tumor model had been valuable [Dewey, R A. et al., *Chronic brain inflammation and persistent herpes simplex virus 1 thymidine kinase expression in survivors of syngeneic glioma treated by adenovirus-mediated gene therapy: implications for clinical trials, Nat Med,* 5:1256-63 (1999)], the failure of single therapeutic strategies in increasing survival of human glioblastoma patients suggested that novel therapeutic strategies and a more stringent preclinical model was necessary. Thus, a new model of brain tumors was needed; a model in which conventional experimental strategies would fail. Injecting rather large experimental brain gliomas occupying most of a rat's hemisphere rendered therapies effective in eliminating small tumors completely ineffective.

A consideration of the limitations of the brain in stimulating adaptive immune responses against brain gliomas led to the idea of combining HSV1-TK/GCV with a potent differentiating and recruiting agent for DCs. The combined approach provided a highly statistically significant prolongation of animal survival for more than six months in a tumor model that would have otherwise killed the tumor bearing rats between days 20-25. The inventors herein show that the mechanism of action of the combined treatment is immune mediated, as the presence of Cyclosporin-A mediated immune-suppression improved survival and dramatically and completely abrogated the beneficial effects of the combined gene therapies.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention Example 1

Adenoviral Vectors

Production and Testing of Biological Activities

RAd Flt3-L (expressing Fms-like tyrosine kinase ligand), RAd 35 (expressing β-galactosidase), RAdTK (expressing HSV-TK), RAd-CD40L, and RAd-IL12 were produced and tested in accordance with various embodiments of the present invention.

RAds were first generation replication defective recombinant adenovirus type 5 vectors expressing the transgenes under the transcriptional control of the human cytomegalovirus intermediate early promoter within the E1 region. RAd 35, an adenovirus encoding LacZ under the control of the hCMV promoter was originally described by Wilkinson & Akrigg [Wilkinson, G. W. et al., *Constitutive and enhanced expression from the CMV major IE promoter in a defective adenovirus vector, Nucleic Acids Res,* 20:2233-9 (1992)] and has been used previously by the inventors [Dewey, R A. et al., *Chronic brain inflammation and persistent herpes simplex virus 1 thymidine kinase expression in survivors of syngeneic glioma treated by adenovirus-mediated gene therapy: implications for clinical trials, Nat Med,* 5:1256-63 (1999); Thomas, C. F. et al., *Gene transfer into rat brain using adenoviral* vectors, *Current Protocols in Neuroscience*, Vol. 4.23.1-4.23.40 (ed. Gerfen, J. N., McKay, R., Rogawski, M. A., Sibley, D. R. and Skolnick, P.) 4.23.1-4.23.40 (John Wiley and Sons, New York, New York, N.Y., 2000); Morelli, A. F. et al., *Neuronal and glial cell type-specific promoters within adenovirus recombinants restrict the expression of the apoptosis-inducing molecule Fas ligand to predetermined brain cell types, and abolish peripheral liver toxicity, J Gen Virol,* 80:571-83 (Pt 3) (1999); Thomas, C. F. et al., *Acute direct adenoviral vector cytotoxicity and chronic, but not acute, inflammatory responses correlate with decreased vector-mediated transgene expression in the brain, Mol Ther,* 3:36-46 (2001)]. RAdTK has been previously described [Dewey, R A. et al., *Chronic brain inflammation and persistent herpes simplex virus 1 thymidine kinase expression in survivors of syngeneic glioma treated by adenovirus-mediated gene therapy: implications for clinical trials, Nat Med,* 5:1256-63 (1999); Cowsill, C. et al., *Central nervous system toxicity of two adenoviral vectors encoding variants of the herpes simplex virus type 1 thymidine kinase: reduced cytotoxicity of a truncated HSV1-TK, Gene Ther,* 7:679-85 (2000); Thomas, W. S. et al., *There is a limited critical period for dopamine's effects on D1 receptor expression in the developing rat neostriatum, Brain Res Dev Brain Res,* 111:99-106 (1998); Zermansky, A. J. et al., *Towards global and long-term neurological gene therapy: unexpected transgene dependent, high-level, and widespread distribution of HSV-1 thymidine kinase throughout the CNS, Mol Ther,* 4:490-8 (2001)] and RAd0 carries no transgene and was used in the studies to control for total viral load [Southgate et al., 2000]. RAdFlt3L was generated by cloning the Flt3L cDNA (provided by Immunex) into the unique BamHI cloning site of the pAL 119 shuttle vector. The shuttle vector was then co-transfected with the E1-deleted adenoviral vector plasmid PJM17 (obtained from Microbix Biosystems; Toronto, Canada) into the human embryonic kidney HE 93 cell line. The presence of the transgenes within the RAds was tested by restriction analysis of the viral DNA and by analysis of protein expression using immunocytochemistry [Southgate et al., 2000]. The methods for adenoviral generation, production, characterisation, scale up, and viral vector purification have been previously described [Cserr, H. F. et al., *Afferent and efferent arms of the humoral immune response to CSF-administered albumins in a rat model with normal blood-brain barrier permeability, J Neuroimmunol,* 41:195-202 (1992); Shering, A. F. et al., *Cell type-specific expression in brain cell cultures from a short human cytomegalovirus major immediate early promoter depends on whether it is inserted into herpesvirus or adenovirus vectors, J Gen Virol,* 78:445-59 (1997); Southgate, T. et al., *Gene transfer into neural cells in vivo using adenoviral vectors, Current Protocols in Neuroscience,* Vol. 4.23.1-4.23.40 (ed. Gerfen, C. R, McKay, R, Rogawski, M A., Sibley, D. R, Skolnick, P.) 4.23.1-4.23.40 (John Wiley and Sons, New York, New York, N.Y., 2000)]. Titrations were carried out in triplicate and in parallel for all viruses by end point dilution, cytopathic effect (cpe) assay, with centrifugation of infected 96 well plates as described in detail by Nyberg-Hoffman et al. [Southgate, T. et al., *Gene transfer into neural cells in vivo using adenoviral vectors, Current Protocols in Neuroscience,* Vol. 4.23.1-4.23.40 (ed. Gerfen, C. R, McKay, R, Rogawski, M A., Sibley, D. R, Skolnick, P.) 4.23.1-4.23.40 (John Wiley and Sons, New York, New York, N.Y., 2000); Nyberg-Hoffman, C. et al., *Instability of adenoviral vectors during transport and its implication for clinical studies, Nat Med,* 5:955-7 (1999)]. The titre determined was $6.55 \times 10^{11}$ i.u./ml for RAd-Flt3-L, $3.25 \times 10^{11}$ i.u for RAd TK and $1.64 \times 10^{11}$ i.u for RAd35. All viral preparations were screened for the presence of replication competent adenovirus [Dion, L. D. et al., *Supernatant rescue assay vs. polymerase chain reaction for detection of wild type adenovirus-contaminating recombinant adenovirus stocks, J Virol Methods,* 56:99-107 (1996)] and for LPS contamination, using the *Limulus amebocyte* gel clot assay (obtained from Biowhittaker; UK)[Cotten, M. et al, *Lipopolysaccharide is a frequent contaminant of plasmid DNA preparations and can be toxic to primary human cells in the presence of adenovirus, Gene Ther,* 1:239-46 (1994)]. Virus preparations used were free for RCA and LPS contamination. All relevant adenoviral methods and quality control procedures are described in detail in [Southgate, T. et al., *Gene transfer into neural cells in vivo using adenoviral vectors, Current Protocols in Neuroscience,* Vol. 4.23.1-4.23.40 (ed. Gerfen, C. R, McKay, R, Rogawski, M A., Sibley, D. R, Skolnick, P.) 4.23.1-4.23.40 (John Wiley and Sons, New York, New York, N.Y., 2000)]. Viruses were diluted in sterile saline for injection.

RAds expressing CD40L and IL-12 were produced and have previously been described in detail elsewhere [Sun, Y. et al., *In vivo gene transfer of CD40 ligand into colon cancer cells induces local production of cytokines and chemokines, tumor eradication and protective antitumor immunity, Gene Ther,* 7:1467-76 (2000); Lasarte, J. J. et al., *Different doses of adenoviral vector expressing IL-12 enhance or depress the immune response to a coadministered antigen: the role of nitric oxide, J Immunol,* 162:5270-7 (1999); Godiska, R. et al., *Human macrophage-derived chemokine (MDC), a novel chemoattractant for monocytes, monocyte-derived dendritic cells, and natural killer cells, J Exp Med,* 185:1595-604 (1997)].

The biological activity of Flt3L expressed by RAds was determined by the ability of the secreted proteins to attract mono-derived DCs in a chemotactic migration assay. Conditioned media generated from Cos7 cells infected with an increasing MOI of either RAdMDC or RadFlt3L was used, ranging from no virus, MOI 0 to MOI 1000. The assay involves adding chemoattractant solution and control media to lower wells of the chemotactic chamber. These wells are covered with a polycarbonate filter (pore size 5 mm) and covered with a silicon gasket and top plate. The upper chamber was seeded with 50 µl of cell suspension ($0.7$-$1.5 \times 10^6$/ml). The chamber was then incubated at 37° C., 5 $CO_2$ for two hours. After incubation, the filters were removed, stained, and the cells counted. The results are expressed as the mean number of migrated cells. Conditioned media from cells infected with RAd-FLt3L were 2-6 times more efficient compared to controls in effecting the chemotactic activity of monocyte-derived DCs (results not shown).

Example 2

Animal Models

Macroscopic Tumor Model

Male Lewis rats (225-250 g in body weight) were anaesthetized with halothane and placed in a stereotaxic frame that had been modified for use with inhalational anesthesia [Thomas, C. F. et al., *Acute direct adenoviral vector cytotoxicity and chronic, but not acute, inflammatory responses correlate with decreased vector-mediated transgene expression in the brain, Mol Ther,* 3:36-46 (2001)]. Animals were injected in the left striatum (1 mm forward from bregma, 3 mm lateral and ventral 4 mm from the dura) with $5 \times 10^3$ CNS1 cells [Dewey, R A. et al., *Chronic brain inflammation and persistent herpes simplex virus 1 thymidine kinase expression in* survivors of syngeneic glioma treated by adenovirus-mediated gene therapy: implications for clinical trials, Nat Med, 5:1256-63 (1999)]. The cells were administered in a volume of 3 ml using a 10 ml-hamilton syringe. For each injection a small pocket was created before the deposition of cells in the striatum. This involved moving the needle 0.2 mm below the stated coordinates, holding for 1 minute before moving up to the stated coordinates, and slowly injecting all the cells over a period of 3 minutes. The needle was left in place for a further 5 minutes before being removed. Viruses were injected into the tumor 3 days post CNS1 cell implantation, using the same anterior and lateral coordinates. Doses of $1\times10^7$ i.u and $8\times10^7$ i.u RAdFlt3L were injected intratumorally. RAd35 and saline were used as controls. Animals were monitored daily, and rats showing morbidity were perfused fixed with heparinised Tyrode followed by 4% paraformaldehyde in PBS. The brains were removed for histological analysis. Animals surviving treatment were allowed to survive for up to three and six months in order to assess the efficiency and impact of the treatment within the brain.

Example 3

Large Tumor Model

Male Lewis rats (225-250 g in body weight) were injected in the left striatum (1 mm forward from bregma, 3 mm lateral and ventral 4 mm from the dura) with $5\times10^3$ CNS1 cells as described above. Doses of $8\times10^7$ i.u of either RAdTK (RAd128) or RAdFlt3L were injected intratumorally 3 days, 6 days and 10 days post tumor implantation, in order to determine at which time point post tumor implantation these treatments would fail (i.e., animals would die within 30 days). Animals were monitored daily, and animals showing morbidity were perfused-fixed and the brains removed for histological examination. Simultaneously, to determine the size of tumours at the time of treatment, animals were perfused fixed 3 days, 6 days and 10 days post CNS1 implantation. 40 mm-thick serial brain sections were cut using a vibrotome. The section in which the tumor fills the largest area of the striatum was used for the calculation of tumor size. To determine the size of the tumors at each point, the following equation, which determines the volume of an ovoid, was used: $4/3p_{abc}$, where a is the shortest radius of cross-sectional face of the tumor; b is the largest radius of the cross-sectional face of the tumor; and c is the total thickness of the tumor in mm. The ten day post CNS1 cell implantation macroscopic tumor model was used to assess the efficacy and side effects of combined HSV1-TK and immune-mediated gene therapeutic approaches as described below.

Ten days post CNS1 cell implantation, rats were injected intratumorally with $1\times10^7$ i.u RAdTK combined with either $1\times10^7$ i.u of either RAdFlt3L, RAdCd40L, RAdIL-12, or RAd0. On day eleven following the injection of the virus, 25 mg/kg ganciclovir (obtained from Cymvene; Roche; Welwyn Garden City, UK) was injected intraperitoneally twice daily for seven days.

Each of the viruses combined with RAd0 was used as experimental controls. All animals including controls received ganciclovir. Animals were monitored daily for any signs of morbidity, and were perfused-fixed and the brains and spinal cords removed for histological analysis. Long term survivors were allowed to survive up to six months.

Example 4

Cyclosporin-A Treatment

In experiments involving immunosuppression, animals were immunosuppressed seven days following CNS1 cell implantation. Animals received 10 mg/kg of Cyclosporine A (obtained from Neoral; Sandoz)/300 µl olive oil given orally by gavage twice daily until the termination of the experiment. A separate group of animals were given 300 µl olive oil only and were the negative controls for the immunosuppression experiments.

Example 5

Brain Immunohistochemistry

40 µm thick coronal sections were cut through the striatum using a vibratome. Free-floating immunohistochemistry was performed to detect inflammatory and immune cell markers. Endogenous peroxidase was inactivated with 0.3% hydrogen peroxide, and sections were blocked with 10% horse serum (obtained from Life Technologies; Paisley, Scotland) before incubating overnight with primary antibody diluted in PBS containing 1% horse serum and 0.5% Triton X100. The primary antibodies and the dilutions at which they were used were ED1 (activated macrophages/microglia cells, 1:1,000; obtained from Serotec), anti-CD8 (cytotoxic T lymphocytes and NK cells, 1:500; obtained from Serotec), Anti-CD8b (β-chain of MHCI restricted T cells, 1:2000 dilution; obtained from Becton Dickenson), Anti-CD161 (receptor on NK cells, 1:2000 dilution; obtained from Becton Dickenson), anti OX62 (DCs, 1:20; obtained from Serotec) and anti-myelin basic protein (1:2,000; obtained from Dako). All primary antibodies were mouse monoclonal anti-rat, except for anti-myelin basic protein, which was rabbit polyclonal anti-human. Secondary antibodies were biotinated rabbit anti-mouse or biotinated swine anti-rabbit (Dako), diluted 1:200 in 0.5% Triton X100 with 1% horse serum, and were detected by using the Vectastain Elite ABC horseradish peroxidase method (obtained from Vector Laboratories). After developing with diaminobenzidine and glucose oxidase, sections were mounted on gelatinised glass slides and were dehydrated through graded ethanol solutions before coverslipping.

Example 6

Microscopy

Tissues were observed with the Olympus (AH2-RFL) microscope, and images captured by standard photographic techniques. Low and high magnification images presented were photographed at either 1×4, or 10×2.5 respectively. Morphology analysis involved higher magnifications, 40×2.5, or 60×2.5 or 10×2.5. Images of whole brain sections were taken at 1×2.5.

Example 7

Spinal Cord Immunohistochemistry

Animals were perfused with 4% paraformaldehyde in 0.1 M phosphate buffer. The spinal cord was dissected and 12 to 14 blocks from all levels of the cord were routinely embedded in paraffin. Five micrometer thick sections were stained with hematoxylin & eosin, with Luxal fast blue myelin stain and with Bielschowsy's silver impregnation for axons. Adjacent serial sections were subjected to immunocytochemistry for T-cells (W3/13; obtained from Seralab; UK) and macrophages (ED 1; obtained from Serotec). Binding of primary antibodies was visualized with a biotin avidin system, using biotinylated species specific anti-mouse immunoglobulin (obtained from Amersham; UK) and avidin peroxidase (obtained from Sigma; St. Louis, Mo.). Peroxidase reaction was developed with diaminobenzidine (obtained from Fluka; Switzerland).

Example 8

Statistical Analysis

Survival data were analysed by Kaplan-Meier estimator analysis, and compared using the log rank tests were performed using the SPSS software and PRISM software.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of prolonging the survival of a mammal that has a brain tumor, comprising:
   providing a quantity of a first viral vector encoding thymidine kinase (TK) operably linked to a first promoter;
   providing a quantity of a second viral vector encoding Fms-like tyrosine kinase 3 ligand (Flt3L) operably linked to a second promoter;
   co-administering a therapeutically effective amount of the quantity of the first viral vector encoding TK operably linked to the first promoter and the quantity of the second viral vector encoding Flt3L operably linked to the second promoter directly into the brain tumor in the mammal; and
   administering a therapeutically effective quantity of systemic ganciclovir to the mammal, wherein the TK and Flt3L are expressed in the brain tumor, wherein the brain tumor is macroscopic at the time of initial treatment, and wherein survival of the mammal is prolonged for at least six months.

2. The method of claim 1, wherein the first and second viral vectors are independently selected from the group consisting of recombinant adenoviral vectors, recombinant adeno-associated viral vectors, herpes simplex virus type 1 vectors, and lentiviral vectors.

3. The method of claim 1, wherein the viral vector encoding TK operably linked to the first promoter is a recombinant adenoviral vector.

4. The method of claim 1, wherein the viral vector encoding Flt3L operably linked to the second promoter is a herpes simplex virus type-1 vector.

5. The method of claim 1, wherein the brain tumor is a glioma.

6. A method for prolonging the survival of a mammal that has a brain tumor, comprising:
   providing a quantity of a viral vector encoding a TK gene operably linked to a promoter;
   providing a composition comprising Flt3L protein;
   co-administering a therapeutically effective amount of the quantity of the viral vector encoding the TK gene operably linked to the promoter and the composition comprising Flt3L protein directly into the brain tumor in the mammal; and
   administering a therapeutically effective quantity of systemic ganciclovir to the mammal, wherein TK is expressed in the brain tumor and Flt3L protein is present in the brain tumor, wherein the brain tumor is macroscopic at the time of initial treatment, and wherein survival of the mammal is prolonged for at least six months.

7. The method of claim 6, wherein the composition further comprises a pharmaceutically acceptable carrier.

8. The method of claim 6, wherein the viral vector is selected from the group consisting of recombinant adenoviral vectors, recombinant adeno-associated viral vectors, herpes simplex virus type 1 vectors, and lentiviral vectors.

9. The method of claim 6, wherein the viral vector is a recombinant adenoviral vector.

10. The method of claim 6, wherein the brain tumor is a glioma.

11. An animal model for brain cancer, comprising a non-human mammal, wherein the non-human mammal carries in at least a portion of the cells of its brain at least one exogenous TK gene operably linked to a first promoter and at least one exogenous Flt3L gene operably linked to a second promoter, wherein the non-human mammal carries a macroscopic tumor in its brain.

12. The method of claim 1, wherein the brain tumor is a glioblastoma.

13. The method of claim 6, wherein the brain tumor is a glioblastoma.

* * * * *

UNITED STATES PATENT AND TRADEMARK OFFICE
CERTIFICATE OF CORRECTION

PATENT NO.       : 8,420,611 B2                                          Page 1 of 1
APPLICATION NO. : 11/572391
DATED            : April 16, 2013
INVENTOR(S)      : Lowenstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 396 days.

Signed and Sealed this

First Day of September, 2015

Michelle K. Lee
*Director of the United States Patent and Trademark Office*